United States Patent [19]

Zimmerschied

[11] Patent Number: 4,476,710
[45] Date of Patent: Oct. 16, 1984

[54] DETONATION TRANSFER EVALUATION TECHNIQUE

[75] Inventor: Alan B. Zimmerschied, Renton, Wash.

[73] Assignee: The United States of America as represented by the Secretary of the Air Force, Washington, D.C.

[21] Appl. No.: 469,369

[22] Filed: Feb. 24, 1983

[51] Int. Cl.³ ............................................ G01N 33/22
[52] U.S. Cl. ........................................... 73/35; 73/167
[58] Field of Search ................ 73/35, 167; 102/275.12

[56] References Cited

U.S. PATENT DOCUMENTS

| | | | |
|---|---|---|---|
| 2,431,683 | 12/1947 | Biggar | 73/167 |
| 2,934,014 | 4/1960 | Smith et al. | 102/275.12 |
| 3,242,718 | 3/1966 | Berger et al. | 73/35 |
| 3,263,489 | 8/1966 | Schimmel et al. | 73/35 |
| 3,408,855 | 11/1968 | Slykhouse | 73/35 |
| 3,525,250 | 8/1970 | Hurst | 73/35 |
| 3,528,280 | 9/1970 | Ciccone et al. | 73/35 |
| 3,572,095 | 3/1971 | Kowalick | 73/75 |
| 3,577,762 | 5/1971 | Hornbogen | 73/12 |
| 4,334,423 | 6/1982 | Rainis et al. | 73/35 |

Primary Examiner—James J. Gill
Attorney, Agent, or Firm—Donald J. Singer; Stanton E. Collier

[57] ABSTRACT

In order to evaluate competing explosive trains at explosive interfaces, at least one penalty barrier is inserted in the gap between a donor explosive component and an acceptor explosive component. Each of the barriers, if more than one, has a first layer and a second layer. The first layer is selected to have a shock impedance greater than the second layer so that a shock pulse is attenuated to a desired degree. Additional barriers can be added to increase the attenuation. A use of this device allows the shock intensities to be varied without varying wave shape or duration and further allows use of established shock equation of states of materials.

5 Claims, 1 Drawing Figure

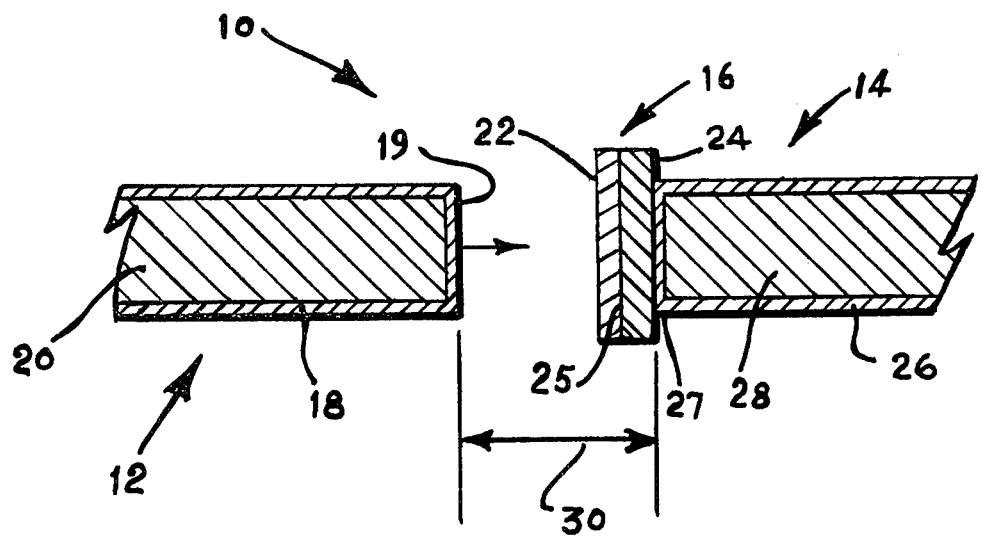

DETONATION TRANSFER EVALUATION TECHNIQUE

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to explosive testing, and more particularly, relates to a method and a device for measuring quantitatively detonation transfer between two explosive components.

Prior attempts to evaluate explosive train performance have employed one of three general approaches:

(1) Firing randomly selected interface assemblies and inferring therefrom the probability of success by attribute (go-nogo) statistical analysis;

(2) By imposing a penalty on the detonation transfer process and using the success ratio as an indicator of transfer capability; or (3) By real-time measurement of transfer phenomena such as transit time of the detonation front or shock pressures.

The attribute statistical analysis requires large numbers of tests to verify the high reliabilities required of detonation transfer systems. As an example, 2,300 successful transfers without any failures is required to verify a 0.999 probability of firing with 90% confidence. The go-nogo evaluation technique is insensitive to performance variations and cannot be used to evaluate the relative performance of competing designs in a transfer system.

Applications of the penalty technique have used air gaps, barriers, and explosive quantity, density, and composition as variable detonation transfer penalties. The resulting performance is evaluated by a statistical analysis such as Bruceton or Probit.

The air gap is the most commonly used penalty in testing. Variations in the air gap change several transfer parameters non-linearly. This non-linearity has not been calibrated to date and prevents extrapolation of probability estimates to the expected gap configuration. The marginal air gap used in the penalty test is normally significantly larger than the design gap and can provide misleading comparison when evaluating different designs.

Variable thickness barriers, also used in the penalty technique, vary several transfer parameters non-linearly and also modify the air gap geometry. Variable aperture barriers modify only the area of particle impact on an acceptor explosive component. The explosive sensitivity to this variable is not well established and this variable is not easily related to expected configurations.

The modifications of explosive densities, quantity, or composition require special component fabrication and must also use additional comparison techniques to relate the modified components to the actual components for probability predictions.

Thirdly, real-time measurements have been limited to very precisely aligned laboratory experiments and have not yet proven suitable for routine testing at the manufacturer's facilities. In addition, the interpretation of real time measurements has not been universally accepted in evaluating competing designs.

The present invention is directed toward providing a technique in which these undesirable characteristics are minimized.

SUMMARY OF THE INVENTION

The present invention overcomes the problems encountered in the past and described in detail hereinabove by providing a detonation transfer evaluation technique and a device which is capable of varying the shock intensity without varying wave shape or duration and is able to use established shock equation of states of materials to determine accurately shock attenuation.

This invention utilizes an accurately defined penalty derived from the shock transmission characteristics across an interface of various materials interposed between two explosive components. The success ratio for each of several penalty levels can be used to determine the probability of successful transfer at the designed conditions.

At an interface in an explosive train used in testing, a donor explosive component and an acceptor explosive component are separated by a given gap. The explosive material in each component is contained within a metal housing. Interposed in the gap between the donor and acceptor is at least one penalty barrier. Each barrier inserted includes two sheet layers of material, only one in contact with the acceptor. By varying the shock impedance of the sheet layers, a high impedance followed by a lower impedance, for example, a net attenuation occurs in the shock stress level. By adding more than one barrier, additional attenuation is obtained when a high impedance layer is followed by a lower impedance layer in each barrier. The thickness of the layers must be sufficient to prevent reflection during the shock pulse and are held constant for all combinations of materials. This constant barrier thickness eliminates the variations in wave shape and pulse duration when the transmitted intensity is varied by changing the materials of the explosive components.

One object of this invention is a detonation transfer evaluation technique that is capable of varying the shock stress intensity without varying the wave shape or pulse duration of that wave.

Another object of this invention is a detonation transfer evaluation technique that is able to use established shock equations of state of the materials.

A further object of this invention is a detonation transfer evalution device that is able to vary shock stress intensity without changing length, shape or pulse duration of a wave.

These and many other objects and advantages of the present invention will be readily apparent to one skilled in the pertinent art from the following detailed description of a preferred embodiment of the invention and related drawing.

BRIEF DESCRIPTION OF THE DRAWINGS

The only FIGURE of the invention is a cross section of a detonation transfer evaluation device used in evaluating detonation transfer characteristics at an explosive interface.

DETAILED DESCRIPTION OF THE PREFERRED EMBODIMENT

Reference is now made to the only FIGURE of the drawings which best illustrates by cross section a detonation transfer interface 10 that has therein an accurately defined penalty.

Detonation transfer interface 10 has a donor explosive component 12 which has a conventional explosive material 20 disposed within a housing 18 with a flat end 19. Housing 18 is typically cylindrically shaped and positioned in a metal frame, not shown, having the explosive train therein. Donor 12 acts as an output at interface 10. An acceptor explosive component 14 is similarly constructed as donor 12 and has a conventional explosive material 28 disposed in a housing 26 which is cylindrically shaped with a flat end 27. Although ends 19 and 27 are described as flat and shown as such in the drawing, other end configurations are clearly possible. For purposes of testing, the shape of ends 19 and 27 must be known and held constant throughout each series of tests so that comparisons are possible from shot to shot with each series. Acceptor 14 acts as an input at interface 10. Donor 12 and acceptor 14 are located a gap distance 30 apart. For testing purposes this may be significantly different than the designed gap. Interposed between donor 12 and acceptor 14 are a plurality of barriers 16, only one shown. Each of barriers 16 is composed of a first layer 22 and a second layer 24. Preferably second layer 24 is in contact with acceptor end 27.

When donor 12 is detonated, end 19 is fragmented and accelerated by shock and gases and traverses gap 30 and impacts acceptor 14 when barriers 16 are not positioned therein. The impact of the fragments on acceptor end 27 generates a shock wave in acceptor explosive material 28. The stress intensity is dependent on the impact velocity and the equations of state of the materials involved. The duration of the shock pulse is dependent on the thickness of the striking fragments which is determined by donor end 19 thickness. The shape of the shock wave is dependent on the size of the impact area on end 27, the simultaneaty of the fragment impacts, and the shape of acceptor end 27. Acceptor explosive material 28 detonates when a shock wave of sufficient stress intensity, duration, and area has penetrated explosive material 28 a finite distance that is an inverse function of the stress intensity.

Each of barriers 16 has first layer 22 composed of a material of given shock impedance, a given sonic velocity, and a given density. Second layer 24 is selected on the basis of shock impedance to provide the desired shock stress intensity. The transmitted shock stress intensity attenuation factor at interface 10 is represented by the following equation:

$$\sigma_{tr}/\sigma_{in} = 2Z_2/(Z_1+Z_2)$$

$\sigma_{tr}$ and $\sigma_{in}$ are the transmitted and incident shock stress levels respectively. $Z_1$ and $Z_2$ are the shock impedance of first layer 22 and second layer 24, respectively. Part of the energy incident at a layer interface 25 is reflected and subsequently delayed by transit time to arrive at explosive material 28 after the primary shock is received.

It can be seen from the above equation that when the materials of layers 22 and 24 have equal impedances, $Z_1 = Z_2$, no attenuation takes place. If the pulse goes from a high impedance to a low impedance, $Z_1 > Z_2$, then $\sigma_{tr}$ divided by $\sigma_{in}$ is less than 1 or if the pulse goes from a low impedance to a high impedance, $Z_2 > Z_1$, then $\sigma_{tr}$ divide by $\sigma_{in}$ is greater than 1. Reflections within barriers 16 having first layer 22 of higher impedance than second layer 25 causes additional attenuation. Additional barriers having alternating high and low impedance can increase the amount of attenuation to a desired level.

First and second layers 22 and 24, respectively, must have a thickness sufficient to prevent reflection during shock impulse and must be held constant for all combinations of material. This constant barrier thickness eliminates the variations in wave shape and pulse duration when the intensity is varied by changing explosive materials 20 and 28, and materials used in containers 18 and 26. Layers 22 and 24 can be composed of plastic materials although not of the same type. Preferably, layer 22 is of the same material as acceptor end 27 and housing 26.

Clearly, many modifications and variations of the present invention are possible in light of the above teachings and it is therefore understood, that within the inventive scope of the inventive concept, the invention may be practiced otherwise than specifically claimed.

What is claimed is:

1. A detonation transfer evaluation method comprising the steps of:
    mounting a donor explosive component opposite an acceptor explosive component so that a gap of a given distance exists between said components;
    selecting at least one penalty barrier;
    placing in said gap at least one of said penalty barriers, said one penalty barrier having a first layer and a second layer in contact with each other, said acceptor explosive component having said second layer of said one penalty barrier in contact therewith at an interface; and
    detonating said donor explosive component to send a shock pulse into said acceptor explosive component through said one penalty barrier.

2. A detonation transfer evaluation method as defined in claim 1 wherein said step of selecting at least one of said penalty barriers comprises selecting the materials and thicknesses of each of said first and second layers.

3. A detonation transfer evaluation method as defined in claim 2 wherein said selecting results in said first layer having a shock impedance greater than said second layer and a barrier thickness sufficient to prevent reflections therein.

4. A detonation transfer evaluation device comprising:
    a donor explosive component mounted in a frame, said donor explosive component including a container to hold explosive material;
    an acceptor explosive component mounted in said frame, said acceptor explosive component including a container for holding acceptor explosive material, said acceptor container having an end opposite said donor explosive component, and said container of said donor explosive component having an end opposite said end of said acceptor explosive component, said donor explosive component and said acceptor explosive component communicating through a gap of a given distance, said donor explosive component and said acceptor explosive component mounted oppositely one another; and
    at least one penalty barrier mounted in said gap, each of said barriers including a first layer in contact with a second layer, one of said barriers adjacent said acceptor explosive component having said second layer contacting said end of said acceptor container.

5. A detonation transfer evaluation device as defined in claim 4 wherein said first layer has a greater shock impedance than said second layer so as to attenuate a shock pulse received by said first layer from the detonation of said donor explosive component.

* * * * *